(12) United States Patent
Yin et al.

(10) Patent No.: US 6,716,450 B1
(45) Date of Patent: Apr. 6, 2004

(54) ENHANCING PROTEIN ACTIVITY THROUGH NANOENCAPSULATION

(75) Inventors: Ray Yin, Newark, DE (US); Tu-Chen Cheng, Timonium, MD (US); H. Dupont Durst, Bel Air, MD (US); Dujie Qin, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/859,260

(22) Filed: May 17, 2001

Related U.S. Application Data

(60) Provisional application No. 60/205,034, filed on May 18, 2000.

(51) Int. Cl.$^7$ .......................... A61K 9/48; A61K 31/74; A61K 31/765
(52) U.S. Cl. ................. 424/451; 424/78.18; 424/78.19; 424/489
(58) Field of Search ............................... 424/451, 78.18, 424/78.19, 489

(56) References Cited

U.S. PATENT DOCUMENTS

| | | | |
|---|---|---|---|
| 5,714,166 A | | 2/1998 | Tomalia et al. |
| 5,919,442 A | * | 7/1999 | Yin et al. ................. 424/78.18 |

\* cited by examiner

Primary Examiner—Thurman K. Page
Assistant Examiner—Blessing Fubara
(74) Attorney, Agent, or Firm—Ulysses John Biffoni

(57) ABSTRACT

Nanocapsules useful for encapsulating bioactive molecules such as proteins are disclosed. These nanocapsules are comprised of branched or hyperbranched polymers and copolymers and have a core-shell structure forming a pocket volume appropriate for complexing and retaining enzymes and other bioactive molecules. The nanoencapsulated bioactive molecule is stable in extreme temperatures and pH, soluble in aqueous or organic solvents, and can be lyophilized to a dry powder for long-term storage without loss of enzyme activity.

24 Claims, 13 Drawing Sheets

NANOCAPSULES

HYDROPHILIC CORE & HYDROPHOBIC SHELL

HYDROPHOBIC CORE & HYDROPHILIC SHELL

AMPHIPHILIC CORE & SHELL

AMPHIPHILIC CORE & HYDROPHOBIC/HYDROPHILIC SHELL

HYDROPHILIC/HYDROPHOBIC CORE & AMPHIPHILIC SHELL

1) Control, 2) Atropine, 3) 2-PAM, 4) 2-PAM+Atropine, 5) 2-PAM+Atropine+Free OPAA-2, 6) 2-PAM+Atropine+OPAA-2 in red blood cells, 7) 2-PAM+Atropine+OPAA-2 in stealth liposomes, 8) 2-PAM+Atropine+OPAA-2 in nanocapsules.

ENHANCING PROTEIN ACTIVITY THROUGH NANOENCAPSULATION

Cross-Reference to Related Applications

This application is a non-provisional continuation of provisional application Serial No. 60/205,034 filed on May 18, 2000.

GOVERNMENT INTEREST

The invention described herein may be manufactured, used, and/or licensed by or for the United States Government.

FIELD OF THE INVENTION

This invention relates generally to polymer nanoencapsulation and, more particularly, to nanocapsule carriers, and a method of using these carriers to enhance and stabilize enzyme reactivity or the reactivity of other encapsulated bioactive molecules.

BACKGROUND OF THE INVENTION

This invention deals with nanoencapsulation and nanocapsules, and a method of using these encapsulation systems to enhance protein/enzyme reactivity. This invention also deals with using polymer nanocapsules to protect proteins and enzymes from inactivation in a variety of harsh environments such as extreme temperatures and pH. In addition, this invention also provides a method for using nanoencapsulation to enhance protein/enzyme reactivity in organic solvents. Finally, the present invention also provides a method of using nanocapsules as controlled-release agents or carriers for drug, protein, and vaccine delivery. Protein/enzyme stabilization is of great interest to a variety of applications including medical diagnostics, bioremediation, environmental clean-up, biocatalysis, and protein delivery. For example, protein or enzyme based medical diagnostic kits that exhibit prolonged shelf-life could improve performance and significantly reduce costs. For environmental decontamination or clean-up applications, the proteins/enzymes utilized need to be able to withstand a variety of harsh environmental conditions. These conditions could range from extreme temperatures (−30 to 60° C.), extreme pHs (pH 1–12), and exposure to both polar and non-polar organic solvents such as methanol, toluene, hexane, and gasoline. For protein delivery applications, the protein carriers or stabilizers have to meet even more stringent requirements. The ideal protein carriers have to be not only non-toxic and non-immunogenic, but also must be able to protect labile proteins against natural deterioration. Moreover, in reality, the larger protein carriers (i.e. greater than 5–7 $\mu$m) are often rapidly cleared from blood by capillary filtration primarily in the lungs. The smaller carriers (i.e. less than 200 nm), although free to circulate through capillaries, still face attacks from the immune system, thus being removed from blood rapidly by phagocytosis. Therefore, those carriers that are capable of generating long-term blood circulation of protein drugs can provide numerous advantages such as enhancing the efficiency of controlled-release drugs, providing site specific protein delivery, as well as reducing the need for repetitive injections.

Currently, protein stabilization has mainly been achieved by: 1) microencapsulation (i.e. with liposomes or water-soluble polymers); 2) bioconjugation (i.e. covalently linking proteins with water-soluble polymers or simply crosslinking proteins to form stable particles); or 3) genetic modification (i.e. genetically altering the protein sequence to make it more stable). However, microencapsulation that utilizes lipid-based micelles often suffers problems such as poor solution stability (especially under extreme temperatures and pH) and difficulty in being freeze-dried. In addition, the size distribution of these micelles is also very broad. The polymer-based microencapsulation, although significantly improving the freeze-drying capability, has very poor solution stability since only physical interactions are present between polymers and proteins. On the other hand, by using polyethylene glycol or oxide (PEG or PEO) modified liposomes (i.e. stealth liposomes) or biodegradable/non-degradable particles (stealth particles), the protein stability can be significantly enhanced. However, the sizes of these carriers are still too large (i.e. in microns) for more efficient and accurate delivery purposes. The bioconjugation of protein molecules with different water-soluble polymers such as PEGs and PEOs may also enhance the stability of proteins. However, this approach is very labor intensive, and, in some cases, the process can denature the proteins resulting in significant activity loss. Through proper genetic modification, the shelf-stability of proteins can be improved dramatically. Unfortunately, in most cases, the protein activity or specificity has also dropped very substantially.

U.S. Pat. No. 5,714,166, entitled "Bioactive and/or Targeted Dendrimer Conjugates," disclosed potential drug carrier applications using dense star polymers. However, this class of polymers is too small for encapsulating large molecules such as proteins, and therefore, does not meet the objective of the present invention. U.S. Pat. No. 5,919,442 entitled "Hyper Comb-Branched Polymer Conjugates," disclosed using larger Combburst polymers as drug carriers. However, no surface functionalization and size effects were described or disclosed as provided by the present invention. In addition, no enabling in vivo protein delivery examples were reported. The preparation of these prior art dendritic polymers also requires a core molecule and well-defined branches that are often more costly to produce through multi-step syntheses, whereas the polymers of the present invention can be obtained by a simple "one-pot" synthesis strategy to generate randomly branched molecular structures without the need of a core molecule.

At present, there is a need for the development of nanoencapsulated enzymes and other nanoencapsulated bioactive molecules having improved stability, improved in vivo delivery characteristics, and the ability to withstand harsh environmental conditions.

SUMMARY OF THE INVENTION

Accordingly, a primary object of the present invention is to provide a nanoencapsulation method for enzymes and proteins.

It is another object of the present invention to provide a method of using this nanoencapsulation approach to formulate more stable protein carrying systems.

It is yet another object of the present invention to use this nanoencapsulation approach to produce protein-carrying formulations that are stable in both aqueous and organic media, as well as extreme pHs and temperatures.

It is still another object of the present invention to use this nanoencapsulation approach to generate nanocapsules that are stable in blood circulation, so that the encapsulated protein can be released in vivo in a controlled manner.

It is a further object of the present invention to provide a simple, inexpensive method of producing nanoencapsulated proteins, enzymes, or other bioactive molecules.

It is another object of the present invention to provide nanocapsules in the 10–500 nm range having an appropriate core size for encapsulation and protection of enzymes or other bioactive molecules.

It is still another object of the present invention to provide nanocapsules having surface functionalization such that solubility of the nanocapsule and reactivity of the encapsulated bioactive molecule is controlled and improved.

Finally, it is another object of the present invention to provide nanocapsules whose structure and characteristics are temperature sensitive so that delivery of encapsulated proteins or other molecules can be controlled by temperature changes.

The foregoing and other objects and advantages of the present invention will hereafter become more fully apparent from the following detailed description. In the description, reference will be made to examples and drawings which form a part hereof, and in which is shown by way of illustration, and not limitation, certain preferred embodiments. Such description does not represent the full extent of the invention, but rather, the invention may be employed according to the full scope and spirit of the invention as defined in the appended claims.

DETAILED DESCRIPTION OF THE PREFERRED EMBODIMENTS

The invention disclosed herein involves nanocapsules with sizes ranging from 10 to 500 nanometers (nm). These nanocapsules, upon appropriate manipulation, are capable of encapsulating or complexing large biomolecules such as proteins, enzymes and DNAs. The resulting biomolecule-containing nanocapsules are stable in both water and organic solvents. Moreover, these nanocapsules can withstand harsh environmental conditions such as extreme temperatures and pH. These nanocapsules are stable in pH 2–12, and in dry powder form the bulk material is stable up to 400° C. under nitrogen, and up to 350° C. in air. The resulting protein nanocapsules exhibit better stability and longer circulation time in the blood stream in vivo, thus releasing proteins in a much more controlled manner than the currently existing protein delivery systems.

Our approach utilizes a simple and inexpensive physical nanoencapsulation strategy that is similar to microencapsulations. In contrast to those unstable and polydisperse micelles that are often in the micron-size region, here the nanocapsules involve-covalently linked nanometer-size capsules that are not only more uniform, but also more stable in a variety of environmental conditions such as extreme pH, temperatures, and organic media. Upon mixing the nanocapsules with peptides and proteins (typically about 1 to 15 nm in diameter) in water, these biomolecules (peptides, proteins etc.) are automatically trapped either inside the nanocapsules or partially complexed within the nanocapsules. Upon lyophilization the folded protein structure is preserved, and the protein reactivity is maintained. After re-dissolving these lyophilized nanocapsules, the protein molecules are re-naturalized and higher protein reactivities have been observed from both in vitro and in vivo tests.

Covalently linked nanometer-sized capsules can be prepared by both divergent and convergent approaches. The divergent approach usually involves multi-step organic synthesis, and this often significantly increases the material's cost. The convergent approach, on the other hand, requires far less synthetic steps. In the case of convergent self-branching polymerizations, it only takes one polymerization step to prepare a reactive hyper-branched dendron, which can then be grafted onto a core moiety to generate more complex macromolecular structures. This core moiety can be a small molecule, a polymer, or a polymeric bead. The resulting nanocapsules are in general fully soluble or dispersible in water or organic solvents. The interior of the nanocapsule can be made to possess a hydrophobic or a hydrophilic core, while their exteriors can be constructed with opposite characteristic layers. In some special cases, nanocapsules that are soluble in both water and organic solvents can also be prepared in order to provide a wide variety of formulation options. Moreover, nanocapsules that exhibit an amphiphilic core and a hydrophobic or hydrophilic exterior, as well as those possessing a hydrophobic or hydrophilic core and an amphiphilic exterior can also be produced. The seven different embodiments of nanocapsules that are utilized in the present invention are schematically depicted in FIG. 1 (note that the last two schematics represent two distinct embodiments each). Due to their unimolecular nature, these nanocapsules are often built with different amounts of layers that are inter-connected through covalent bonds with or without a center core. These interior covalent connections can either be linear, branched, or a combination of both depending on the interior "pocket size" requirements, i.e., the interior volume where the protein or bioactive molecule is encapsulated within the nanocapsule. Different layer numbers can also be defined as generations. For example, the first layer is typically referred to as generation 0, the second is generation 1, the third is generation 2, and the fourth is generation 3, etc., and are usually represented as G0, G1, G2, and G3, respectively.

Figure 1:
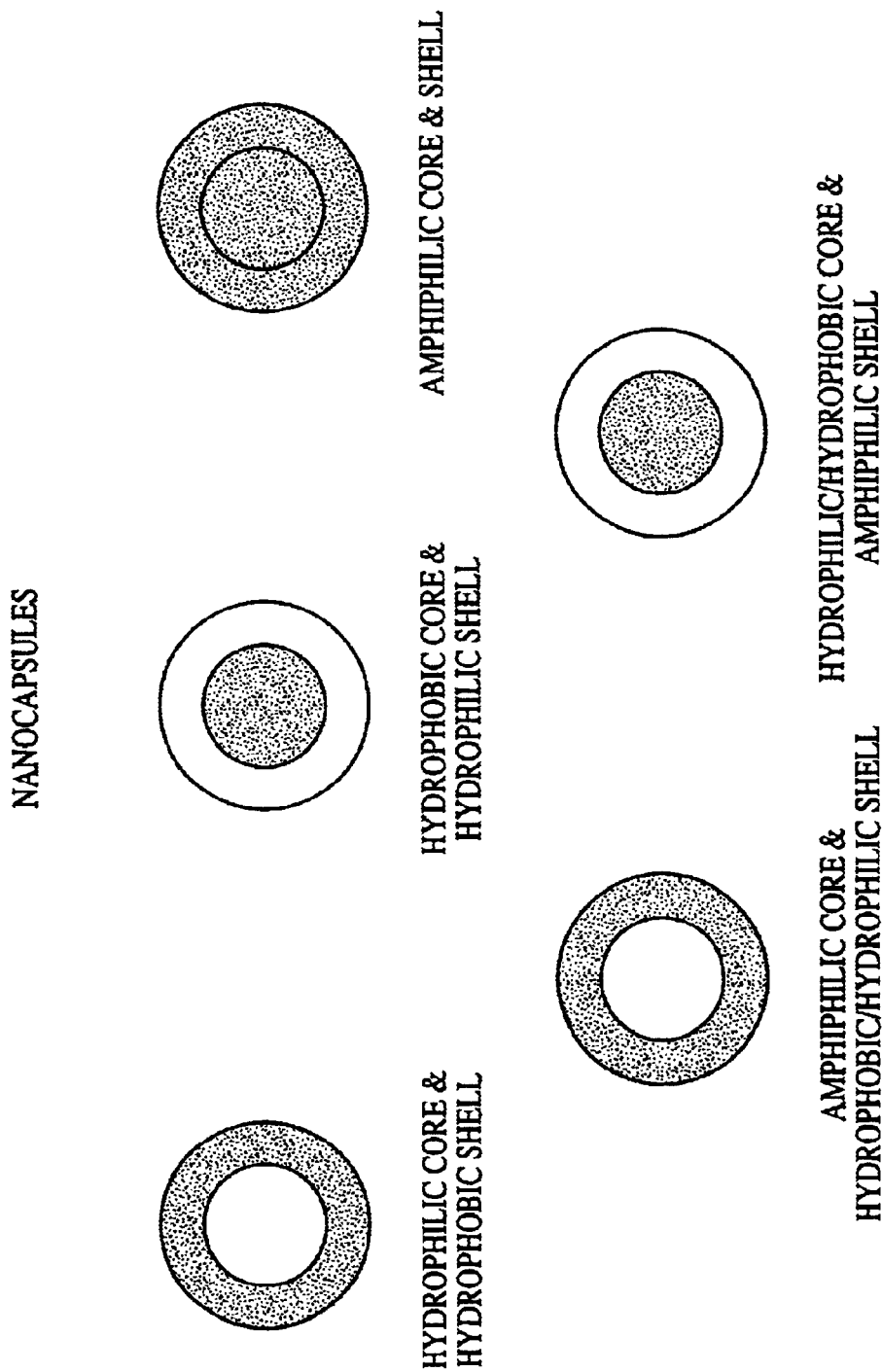
FIG. 1 illustrates several embodiments of various nanocapsules having different surface and core functionalizations including combinations of hydrophilic, hydrophobic, and amphiphilic cores and shells.
Figure 2:
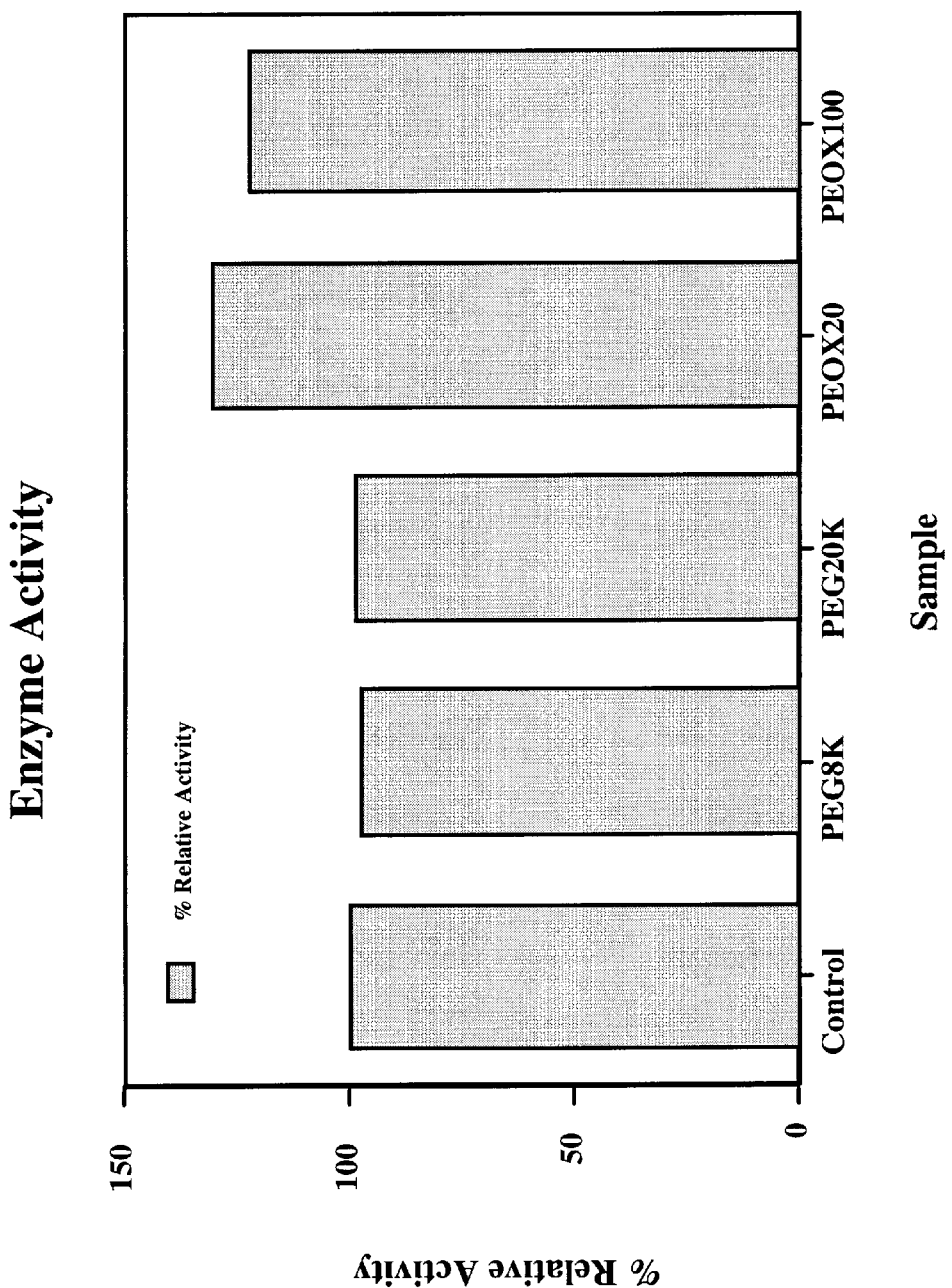
FIG. 2 is a bar graph showing the effects of various linear polymers on enzyme activity where the control is the unencapsulated enzyme.

FIG. 2 shows the relative enzyme activity for a bare enzyme (control) and the activity of the same enzyme when combined with various commercially available linear polymers including polyethylene glycol of 8,000 molecular weight (PEG8K), polyethylene glycol of 20,000 molecular weight (PEG20K), poly(2-ethyloxazoline) of 2,000 molecular weight (PEOX20), and poly(2-ethyloxazoline) of 10,000 molecular weight (PEOX100). Although some of the linear polymers (PEOX20 and PEOX100) showed some improvement in reactivity, these linear. polymer-enzyme complexes fail to provide an encapsulating effect, which protects the enzyme from harsh environmental conditions and solvents and also provides controlled delivery.

Figure 3:
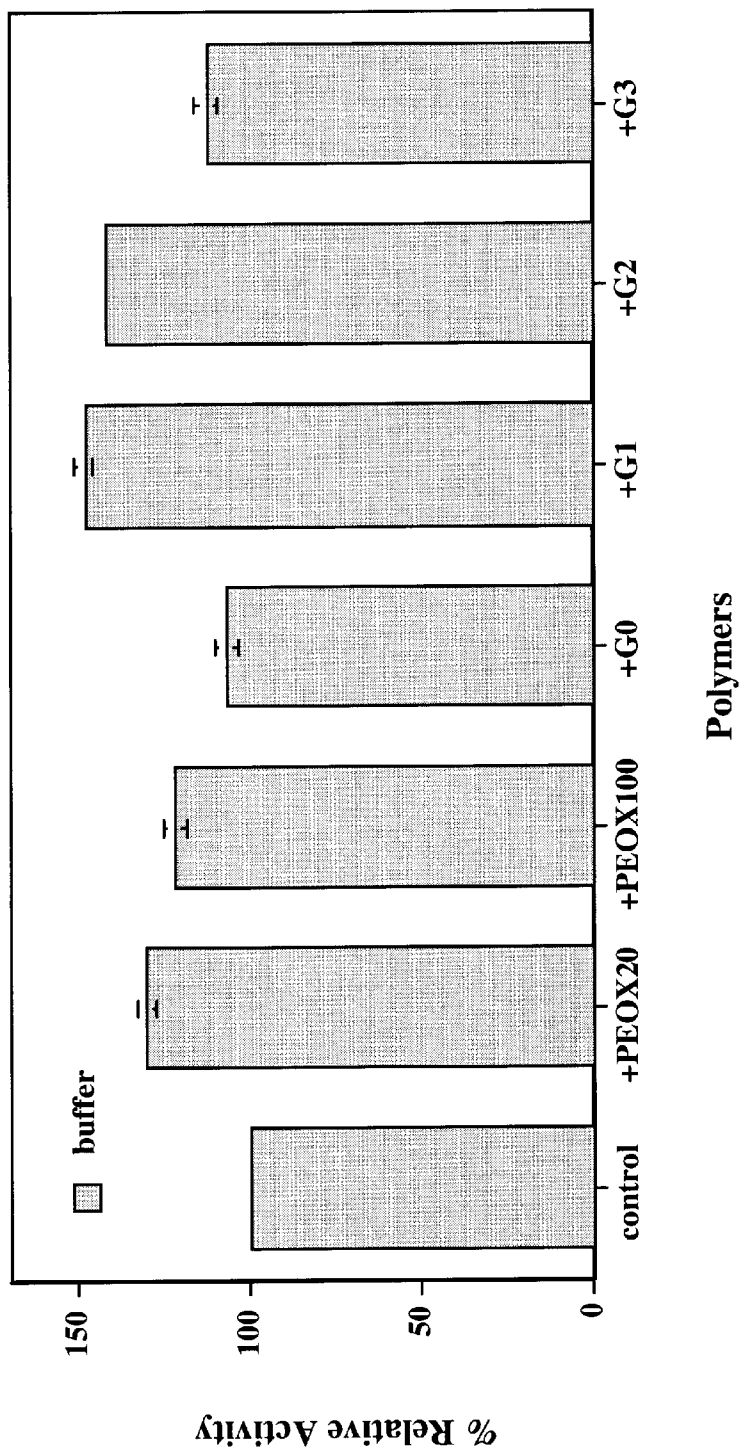
FIG. 3 is a bar graph showing the effects of various polymers on enzyme activity after encapsulation by different nanocapsules with the control being unencapsulated enzyme.

In order to compare different encapsulation effects, a series of polymeric stabilizers that consist of both unimolecular and traditional linear polymers were mixed together with proteins/enzymes, such as the enzyme organophosphonate acid anhydrolase (OPAA) from Alteromonas spJD6.5 in buffer. The gene encoding OPAA from A. spJD6.5 has been cloned and sequenced, see U.S. Pat. Nos. 5,928,927 and 6,080,566, both of which are hereby incorporated by reference herein. The recombinant OPAA, similar to the native enzyme, can hydrolyze a variety of toxic organophosphonate compounds. In this experiment, diisopropylfluorophosphate (DFP) was utilized as a model substrate to measure enzyme activity and to study encapsulation efficacy. Enzymes that possess higher activities will hydrolyze DFP molecules to fluoride ion at faster reaction rates. A fluoride electrode can conveniently measure this effect. In FIG. 3, the control is the bare enzyme while PEOX20 and PEOX100 are linear polymers as discussed earlier, and G0, G1, G2, and G3 represent first, second, third and fourth generation poly(2-ethyloxazoline) nanocapsules. It was found that within the same nanocapsule family, i.e., those consisting of the same chemical compositions but with different numbers of layers, the nanoencapsulation efficacy first increased with layers and reached the maximum at the second layer stage, and then started to decrease, for example, where G1 corresponds to a second layer (generation) poly(2-ethyloxazoline) (PEOX) polymer. This is because in the earlier generations of the PEOX polymers, the surface is very open. Thus, large protein molecules such as OPAA (~60,000 in molecular weight) can easily penetrate into the nanocapsules and form a stable complex due to the presence of ionic, hydrogen bonding, and/or hydrophobic interactions that prevent OPAA from denaturing, thus maintaining structural stability and even enhancing the enzyme catalytic activity. At the same time, the small substrate molecules such as DFP and its hydrolyzed products can still freely diff-use in and out of the nanocapsules. At the second layer stage, i.e., generation 1 of the PEOX polymers, a higher level of enzyme activity was observed, suggesting that the most stable and reactive complexes were formed between this specific nanocapsule and the enzyme OPAA. In contrast, as more layers were added, the exterior becomes more and more congested, thus preventing the enzyme molecules from being encapsulated. As a result, more free enzymes are left outside the nanocapsules, thus resulting in lower enzyme activity. It should be noted that even with this surface congestion, the encapsulated enzymes are still more active than their naked enzyme counterparts. This indicated that some of the OPAA molecules are still partially encapsulated by nanocapsules. In conclusion, the protein encapsulation efficiency is highly dependent on the degree of surface congestion on the nanocapsule. The more surface congested nanocapsules often give poor encapsulation efficiencies. On the other hand, the loosely grafted or randomly hyper-branched polymers generated through one-pot convergent self-branching polymerization tend to encapsulate protein molecules much more effectively.

Figure 4:
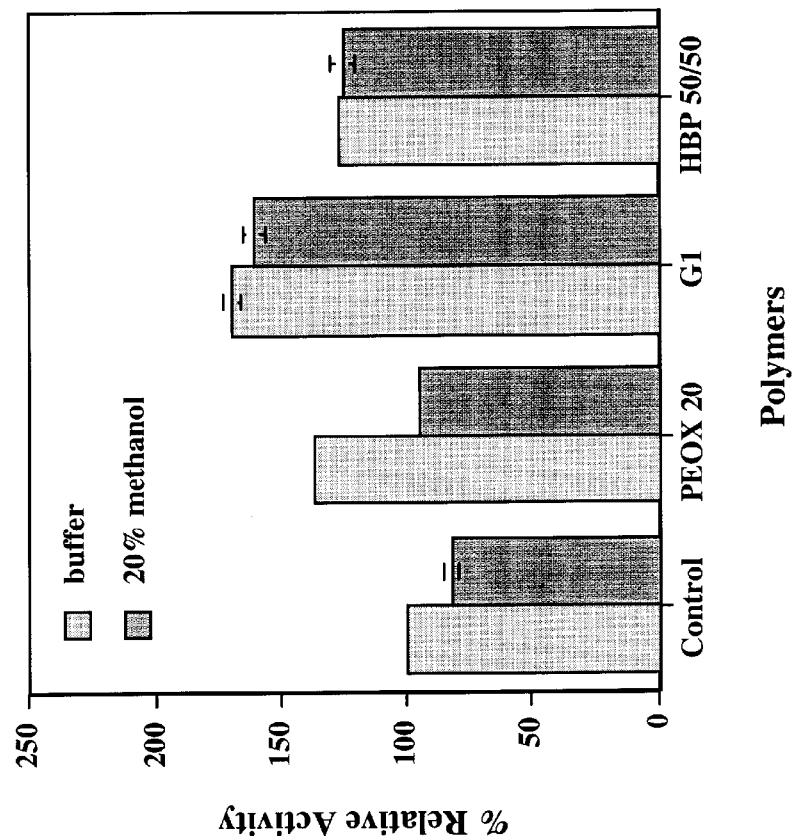
FIG. 4 is a bar graph demonstrating enzyme stability in 20% methanol versus buffer solution for a variety of polymer nanoencapsulated enzymes with the control being the unencapsulated enzyme.

Another interesting observation also shown is that linear polymers such as poly(2-ethyloxazoline) (PEOX20 and PEOX100 shown in FIGS. 2 and 3) and polyethyleneoxide (PEO) polymers with molecular weights between about 2,000 and 10,000 also enhance the enzyme reactivity. This suggests that physical interactions between enzymes and linear PEOX or PEO polymers were also present. For example, hydrogen bonding and/or Van der Waals forces may be causing a physical interaction between the bioactive molecule and the polymer. However, no encapsulation of the enzyme or other bioactive molecule occurs so that upon the addition of methanol to this enzyme solution, a significant loss in activity was observed, while almost no activity loss was seen in the nanoencapsulated enzyme solutions, as shown in FIG. 4. In FIG. 4, the control is again the unencapsulated enzyme, PEOX20 is the linear poly(2-ethyloxazoline) polymer, G1 is the first generation poly(2-ethyloxazoline) nanocapsule, and HBP 50/50 is a hyperbranched poly(2-ethyloxazoline) polymer nanocapsule. This data clearly indicated that in addition to physical interactions the nanoencapsulated enzymes are further protected by the exterior layer structures built in the nanocapsules. Therefore, the nanoencapsulation phenomena described here includes both molecular encapsulation and physical interactions such as ionic bonding, hydrogen bonding, and hydrophobic associations that drive the formation of enzyme-nanocapsule complexes.

Figure 5:
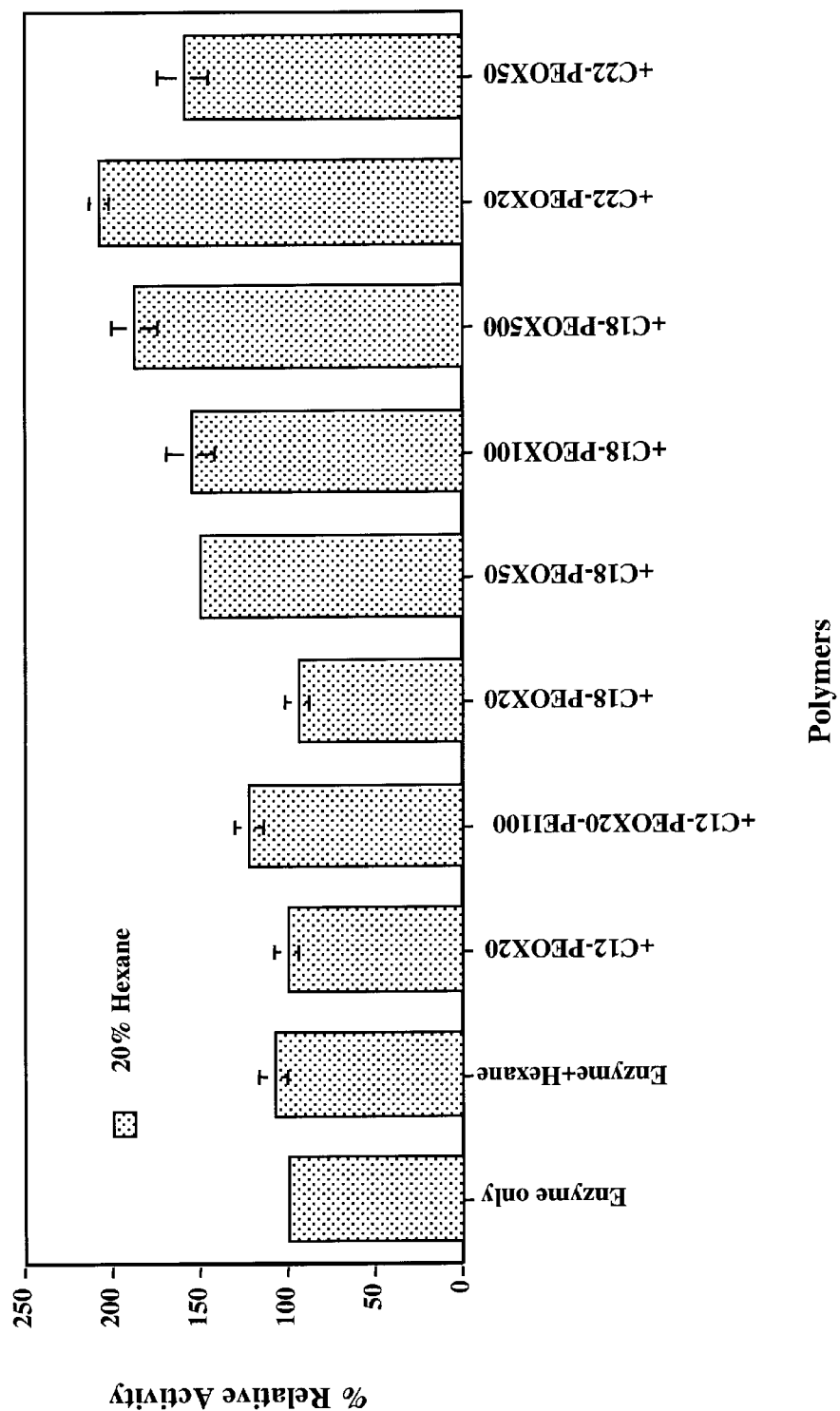
FIG. 5 is a bar graph demonstrating enzyme stability in 20% hexane with a variety of surface functionalized polymer nanocapsules.

With proper modification of the exterior surfaces of nanocapsules, the enzyme activity can not only be stabilized, its activity can also be enhanced in non-polar organic solvents such as hexane. Referring now to FIG. 5, the enzyme activity in the nanocapsules increased with the length of the exterior hydrocarbon chains of the polymeric stabilizers. For example, with C12 exterior modified nanocapsules, i.e., surface modification of hyperbranched PEOX polymers with a 12-hydrocarbon chain at termini, the activity is about the same or slightly lower than the naked enzymes in a hexane-water mixture. However, when the exterior was modified with C18 and C22 (18 and 22 hydrocarbon-chain molecules), much higher reactivity were observed, with C22-PEOX20 being the highest with a two fold increase over the enzyme only control. This result indicated that the enzyme reactivity can be enhanced by simply changing the nanocapsule surfaces, i.e., through surface functionalization with, for example, hydrocarbon chain molecules.

Figure 13:
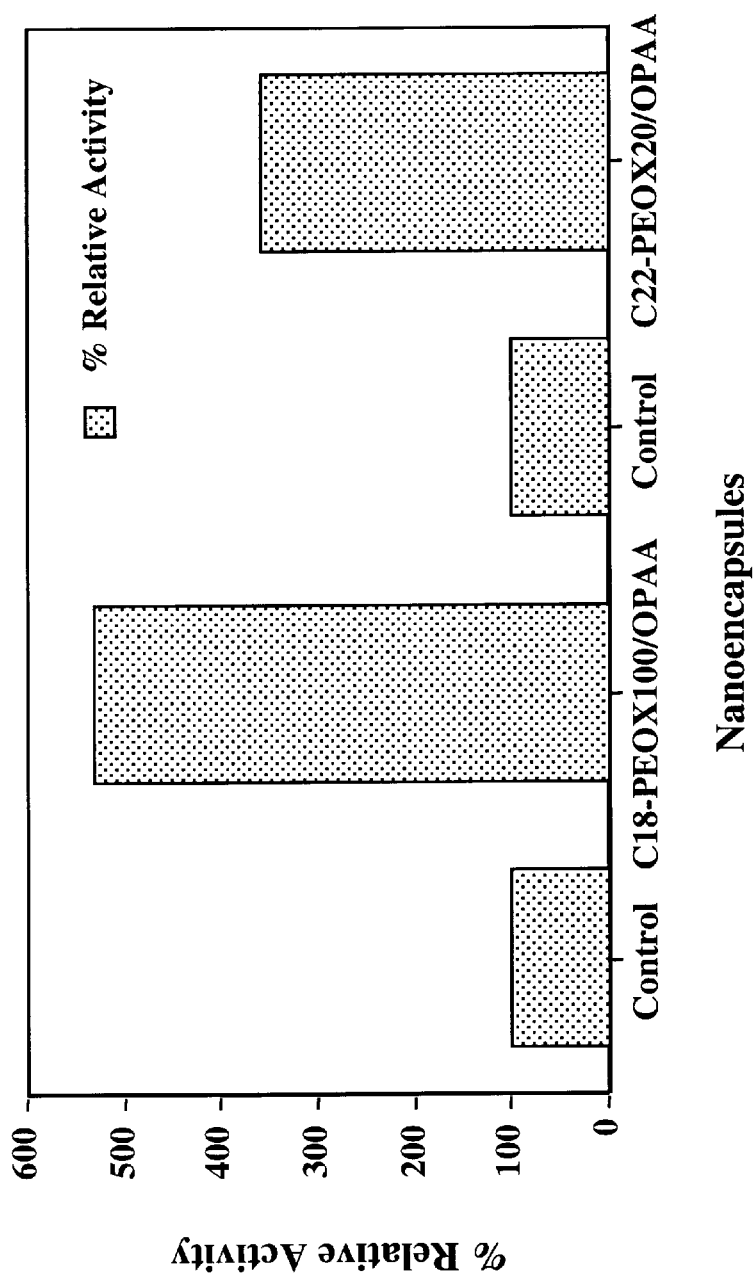
FIG. 13 is a bar graph showing the relative enzyme activity recovery for nanoencapsulated OPAA after lyophilization.

It was also found that the nanoencapsulated enzymes, when stored in dry powder form, could further enhance the long-term shelf-stability of the enzyme when compared with storage as a solution. The long-term stability of the dried nanoencapsulated OPAA enzymes has been studied by storing the matched samples (as dry powders) at both 4° C. and room temperature. Samples were tested periodically during a six-month period. It was found that the unprotected enzyme lost its activity very rapidly, i.e., within hours at room temperature, and slowly deteriorated at 4° C. as well, i.e., degradation in less than a month. In contrast, the nanoencapsulated enzymes are stable up to at least one year without any significant activity loss. The bulk PEOX based nanocapsules are stable at elevated temperatures of 400° C. under $N_2$, and 350° C. under air. FIG. 13 shows the relative activity of various nanoencapsulated OPAA enzymes after lyophilization to produce dry powders.

Figure 6:
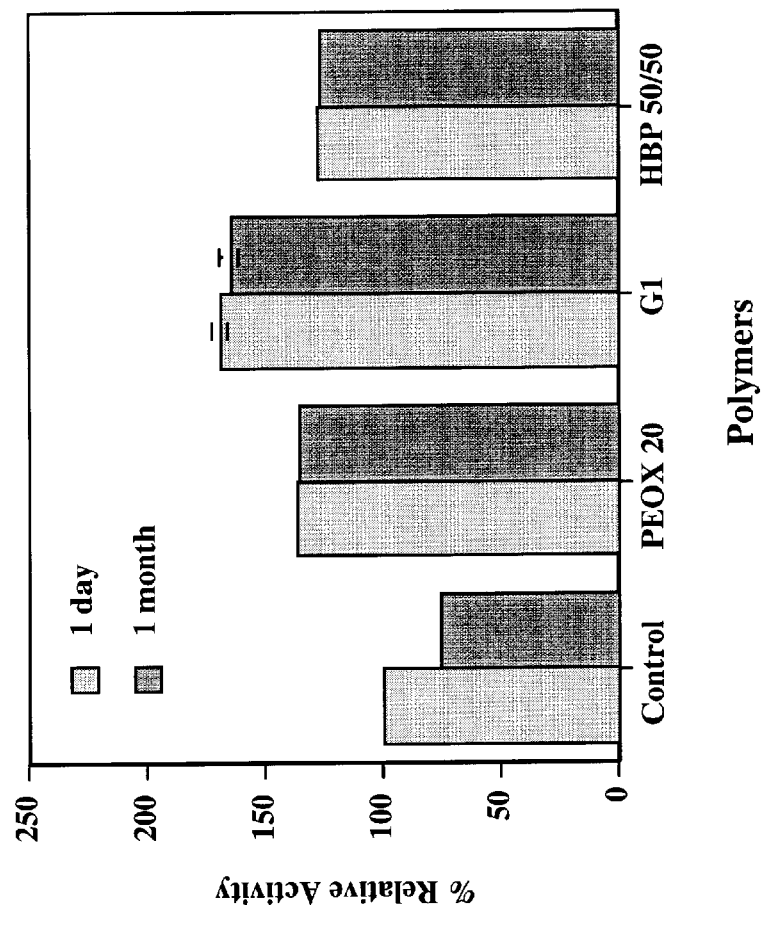
FIG. 6 is a bar graph showing enzyme shelf-life stability in buffer for a variety of nanocapsules for one day versus one month of storage with the control being unencapsulated enzyme.

The solution stability of the nanoencapsulated OPAA enzymes was also investigated in a similar manner. In FIG. 6, a comparison is provided showing the relative activity of the enzyme at one day versus one month for the bare enzyme (control), and for various encapsulated enzymes in buffer. It is clear that the nanoencapsulated OPAA enzymes maintain their activities, while the unencapsulated naked enzyme showed significant activity loss.

Figure 7:
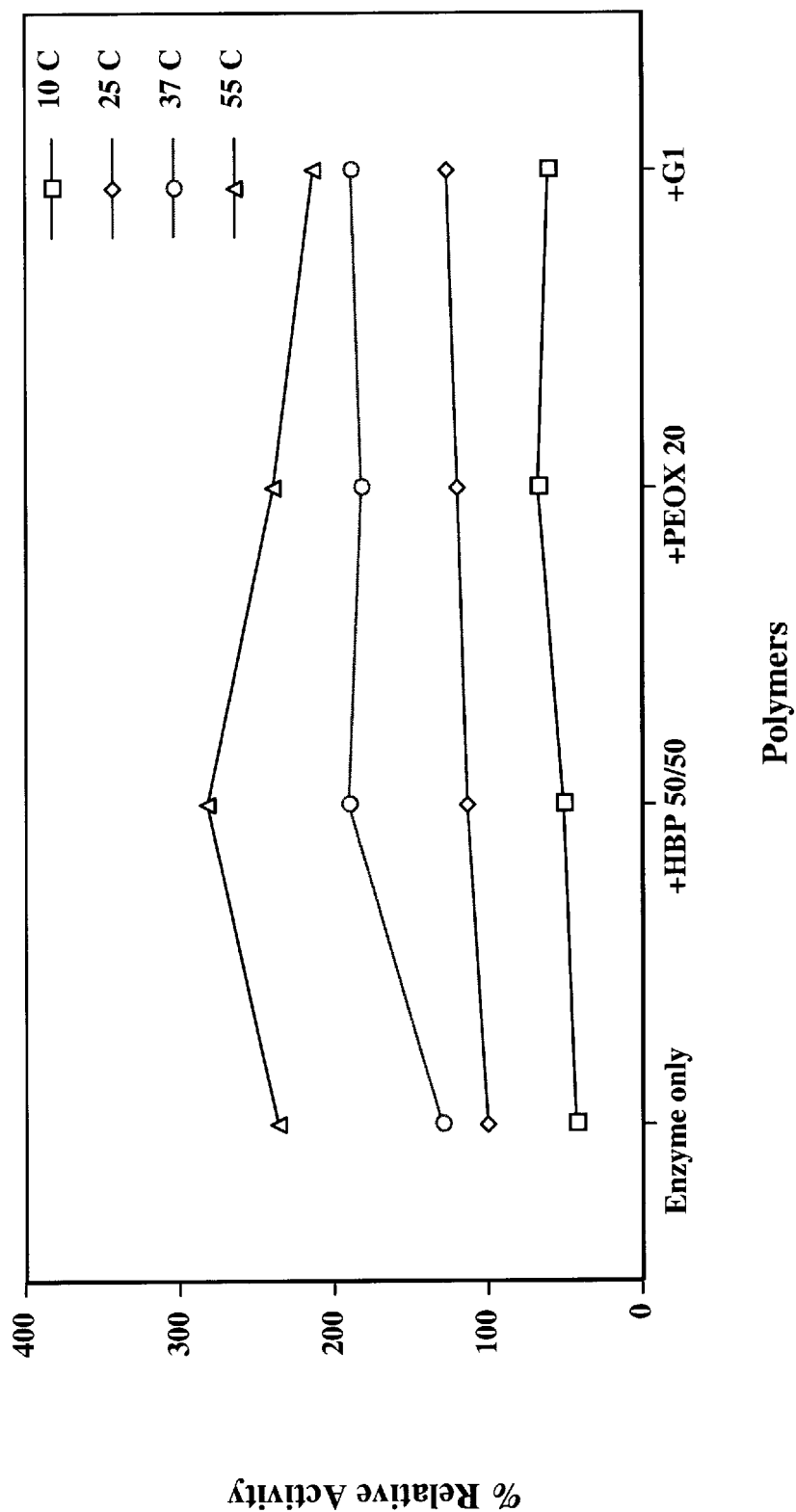
FIG. 7 is a graph showing enzyme stability at different temperatures for various nanoencapsulations.

Referring now to FIG. 7, it was found that similar to the result for the naked enzyme, elevated temperatures (up to 55° C.) also increases enzyme reactivity.

Figure 12:
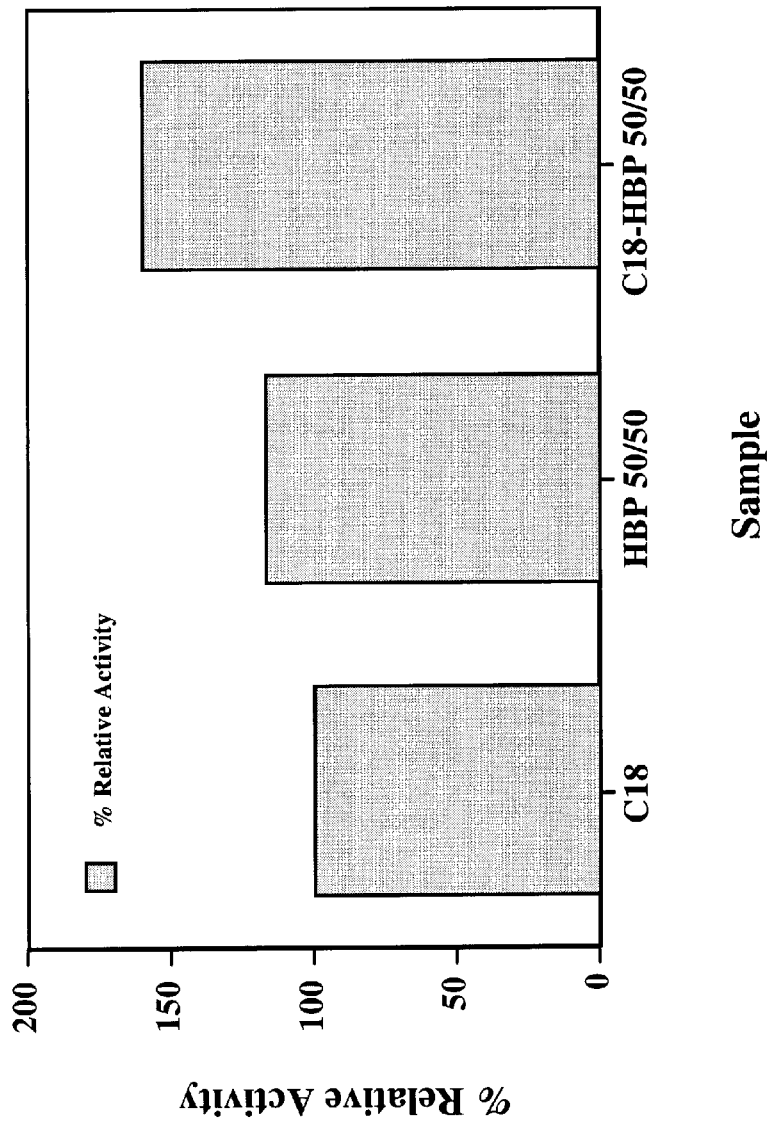
FIG. 12 is a bar graph showing the relative enzyme activity of different dry nanocapsule powders.

As depicted in FIG. 12, when a combination of C18 (hydrophobically) surface modified and amphiphilic nanocapsules (HBP 50/50) are utilized to encapsulate the OPAA enzymes as dry powders, the resulting enzyme activity is much higher than for the individual nanocapsules. This result suggested that a hybrid encapsulation system was more suited for this particular catalytic reaction of the encapsulated OPAA enzyme.

Figure 8:
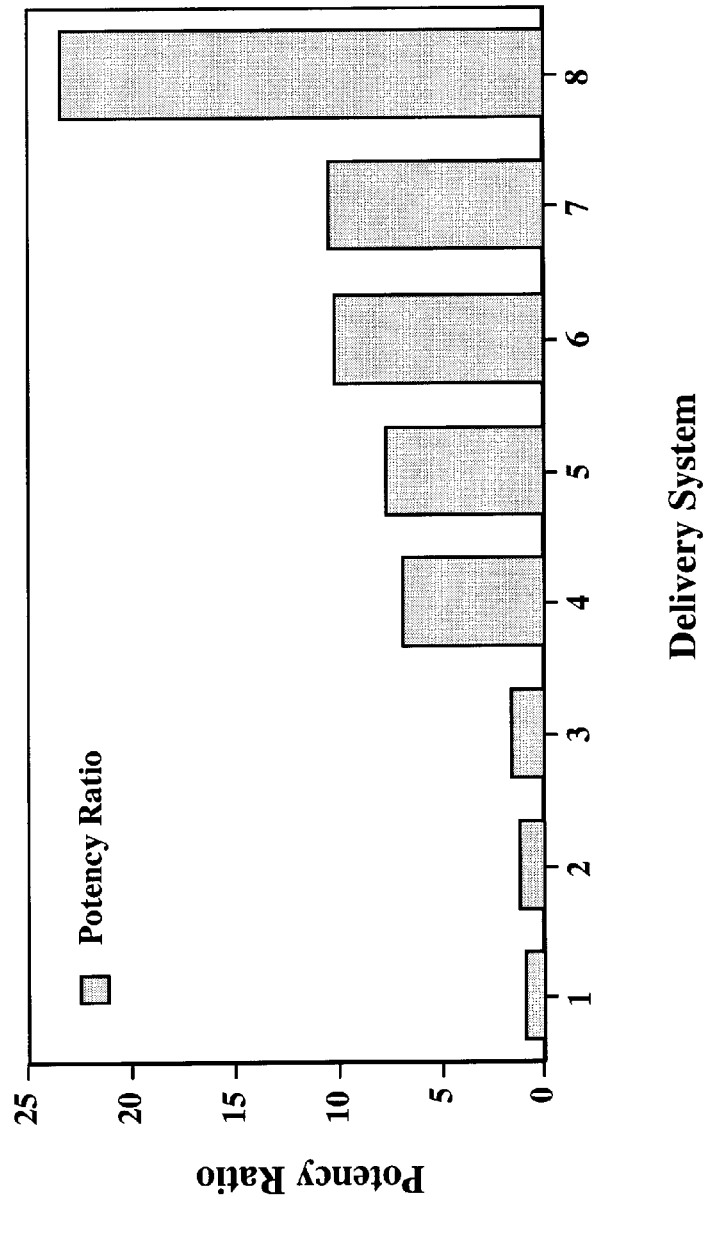
FIG. 8 is a bar graph comparing the protection efficacy (enzyme potency ratio) for a variety of protein delivery systems with the control being a blank.
Figure 9:
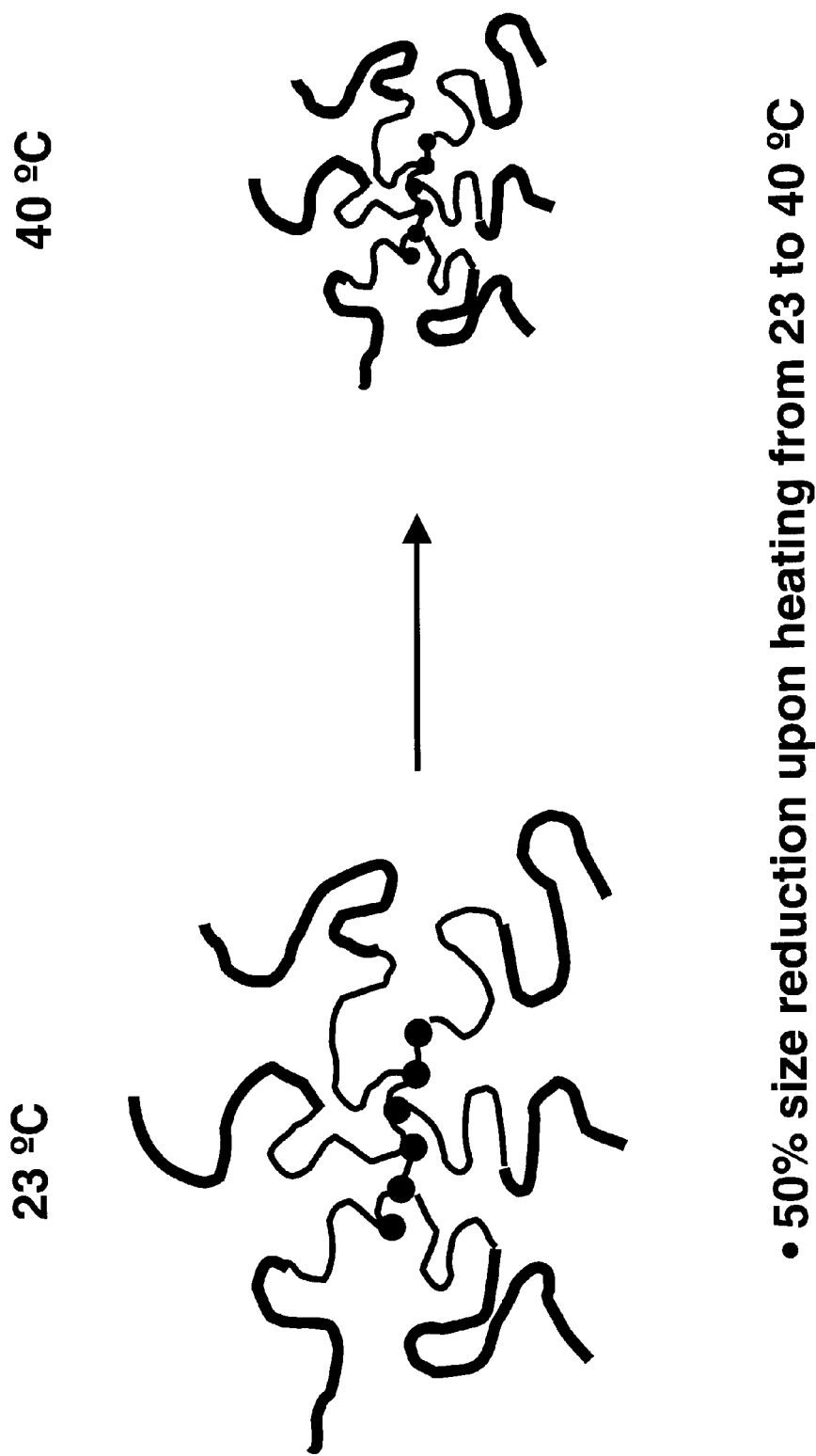
FIG. 9 is a schematic representation showing the temperature sensitivity of a nanocapsule leading to size reduction of the nanocapsule structure.
Figure 10:
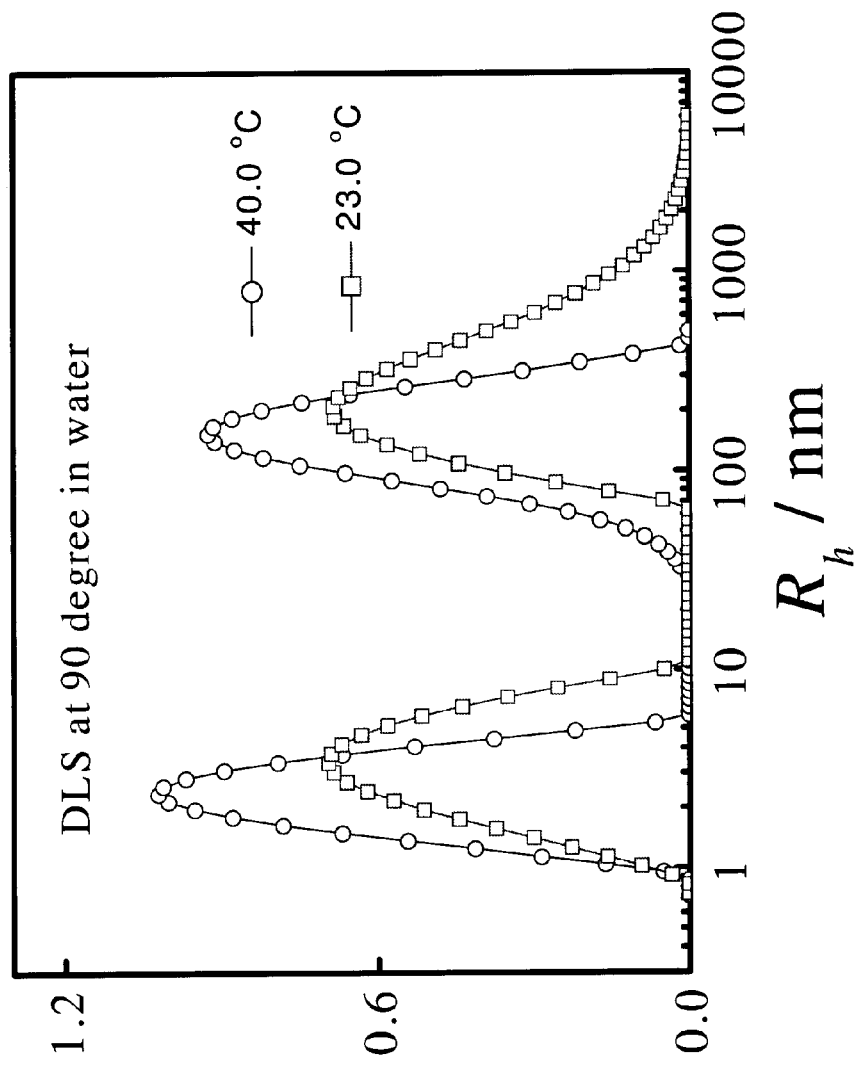
FIG. 10 is a graph showing a change in nanocapsule structure as a result of changing temperature as measured by dynamic light scattering (DLS) at a 90 degree angle in water, where Rh/nm represents hydrodynamic radius in nanometers and the y-axis represents light intensity.
Figure 11:
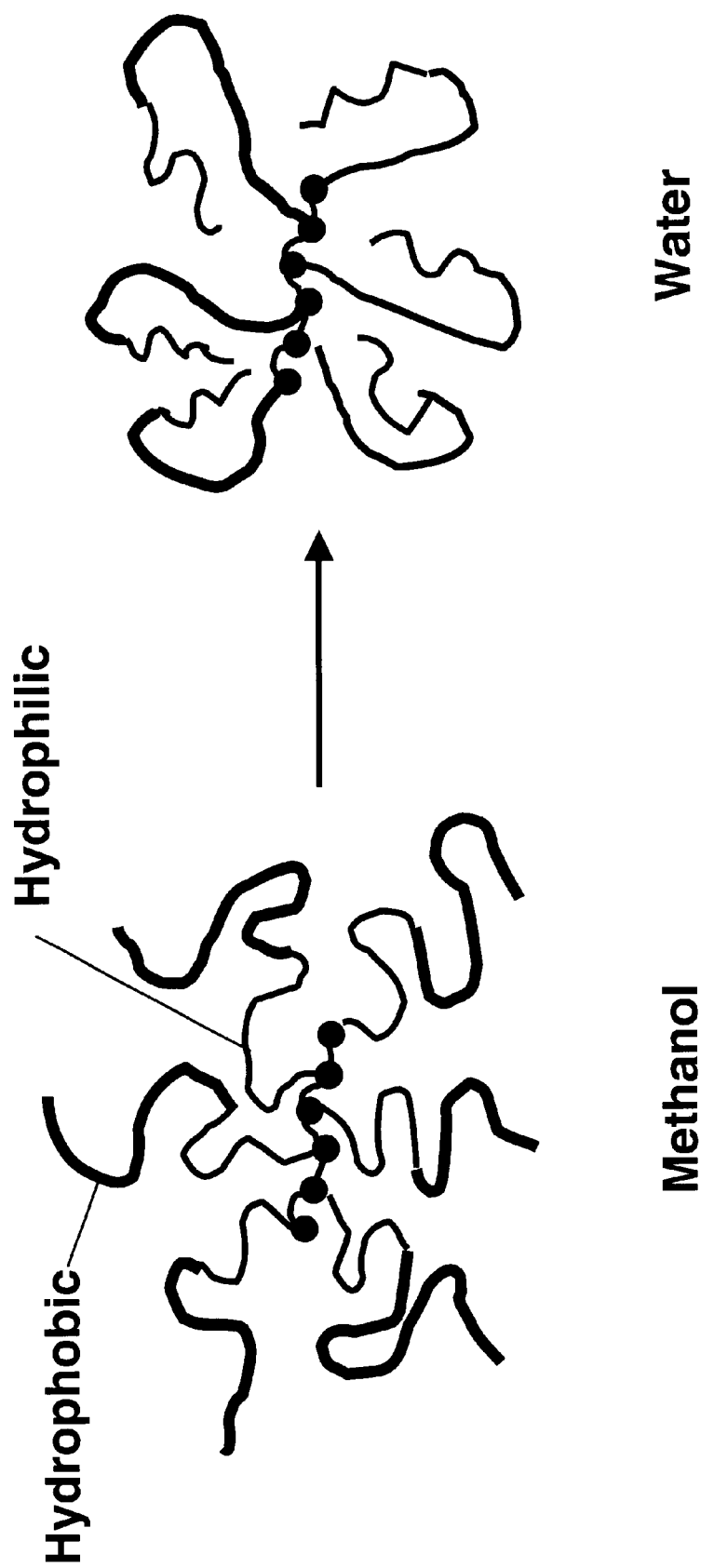
FIG. 11 is a schematic drawing illustrating a change in nanocapsule structure resulting from methanol versus water.

The nanoencapsulation concept has also been tested for protein delivery applications. In this experiment, a group of mice were first exposed to toxic chemicals/materials such as DFP. After the exposure symptoms were developed, different antidote formulations were delivered to the mice through injections. The standard therapeutic antidote for nerve agent exposure is a 2-PAM+Atropine injection. As shown in FIG. 8, a significant increase in protection over the control (here the control is a blank) is achieved when a combination of 2-PAM and atropine is used (bar 1 vs. bar 4). However, upon the addition of naked OPAA enzymes and microencapsulated enzymes using stealth liposomes or red blood cells as carriers to the 2-PAM plus Atropine antidote, only a marginal increase in protection has been observed over the standard antidote mixture. In contrast, when the nanoencapsulated OPAA enzymes in combination with 2-PAM and atropine were used, a dramatic increase in protection has been achieved. At least a three to four-fold activity enhancement over the 2-PAM+Atropine baseline has been obtained as can be seen by comparing bar 4 and bar 8 in FIG. 8.

The physical structure/shape and surface characteristics of the nanocapsules are also dependent upon temperature and the solvent used. For example, as shown schematically in FIG. 9, a 50% size reduction in nanocapsules has been observed upon heating from 23 to 40° C. FIG. 10 shows the change in dynamic light scattering measurements for a nanocapsule as a result of changing temperatures, indicating a change in nanocapsule size. In FIG. 10, $R_h$ is the hydrodynamic radius of the nanocapsule and $f_z(R_h)$ is a function of light intensity. FIG. 11 is a schematic representation of a nanocapsule in methanol and water. In methanol or other organic solvent, the hydrophobic polymer chains of the nanocapsule form the exterior surface making the nanocapsule soluble in methanol, while the interior core of the capsule is hydrophilic in nature. When placed in water, the hydrophobic polymer chains turn inward to form a hydrophobic inner core, while the hydrophilic chains are positioned toward the exterior of the nanocapsule making it soluble in water.

EXAMPLES

Morpholine, $CH_3(CH_2)_nCH_2$—X (n=2–20, X=I, Br, Cl), benzylbromide, and diisopropylethylamine were purchased from Aldrich Chemicals, Inc., and 2-Ethyloxazoline was also obtained from Aldrich. Toluene, methylene chloride, diethyl ether, and methanol were purchased from Fisher Scientific, Inc. 2-Ethyloxazoline, morpholine, diisopropylethylamine toluene, and methylene chloride were stirred over $CaH_2$ and distilled prior to use.

Synthesis of Amphiphilic Nanocapsules

The synthesis of proton initiated HBP500 (Degree of polymerization (DP) 500) is provided as a general procedure for the preparation of PEOX-based nanocapsules. A mixture of toluene sulfonic acid in 500 ml of toluene was azeotroped to remove water with a distillation head under $N_2$ for about 15 min. 2-Ethyloxazoline (100 g) was added dropwise through an addition funnel, and the mixture was allowed to reflux for 12 hours creating solution (I). Upon completion of the polymerization, morpholine was added to the reactive dendrigraft solution (I) in order to terminate the reaction. The bottom layer was re-dissolved in methanol and dried by rotary evaporation and vacuum to give a hyper branched PEOX polymer as a white solid (~99 g, Mp=101,000, MWD=1.73) as determined by SEC.

The nanocapsule-biomolecule conjugates are formed by first dissolving the above PEOX polymer in water or other appropriate solvent, where they become structurally organized, and then simply adding the "active ingredient" biomolecule (such as an enzyme) to the solution where it is automatically encapsulated by the polymer.

The PEOX polymer can also be partially (Soft) hydrolyzed according to the following procedures: To a round bottom flask was added 40 g of HBP500, 20 g of concentrated $H_2SO_4$ (98 wt.), and 200 ml of de-ionized water. The mixture was refluxed for 6 hours, and then neutralized by NaOH until pH was around 10–11. After rotary evaporation of water, the crude product was further purified with methanol and methylene chloride to give a hyper-branched PEI/PEOX copolymer (II) (polyethyleneimine/polyethyloxazoline copolymer).

The higher MW HBPs were prepared through an addition of a PEI/PEOX polymer to the reactive dendrigraft solution (I), followed by immediate addition of diisopropylethylamine (2 eq). The mixture was refluxed for 2 hours, cooled, and the top toluene layer was decanted off. The resulting products were purified through precipitation and rotary evaporation. Other functional PEOX hyper-branched polymers were prepared in a similar manner. All the products were analyzed by SEC, NMR, DSC, and TGA.

Synthesis of Core-Shell (Hydrophobic/Hydrophilic) Nanocapsules

The synthesis of $CH_3$—$(CH_2)_{18}$—HBP100 is provided as a general procedure for the preparation of core-shell nanocapsules. A mixture of $CH_3(CH_2)_{18}CH_2$—Br (3.36 g) in 500 ml of toluene was azeotroped to remove water with a distillation head under $N_2$ for about 15 min. 2-Ethyloxazoline (100 g) was added dropwise through an addition funnel, and the mixture was allowed to reflux between 24 and 48 hours. Upon completion of the polymerization, morpholine was added to the reactive dendrigraft solution (A) in order to terminate the reaction. The crude product was re-dissolved in methanol and then precipitated out from a large excess of diethyl ether. The bottom layer was re-dissolved in methanol and dried by rotary evaporation and vacuum to give a core-shell hyper-branched PEOX polymer as a white solid (101 g, Mw=290,000 as determined by multi angle laser light scattering). The ultra-high MW dendrigrafts were prepared through an addition of a linear PEI100 or a primary amine terminated Starburst dendrimer core (which was dried by azeotropic distillation from toluene) to the reactive dendrigraft solution (A), followed by immediate addition of diisopropylethylamine (2 eq). The mixture was refluxed for 2 hours, cooled, and the top toluene layer was decanted off. The resulting products were purified in the same way. Other hyper-branched polymers such as $C_{12}$-PEOX HBP20, 50, 100, 200, 300, 500, $C_{18}$-HBP20, 50, 200, 300, 500, $C_{22}$-HBP20, 50, 100, 200, 300, 500, and polystyrene-PEOX, etc. functionalized reactive dendrigrafts and their subsequent grafted products/copolymers were prepared in a similar manner. All the products were analyzed by SEC, NMR, DSC, and TGA.

The gene encoding OPAA enzyme has been cloned and sequenced from Alteromonas spJD6.5. Sequence and biochemical analysis of the cloned enzyme has established OPAA to be a prolidase, a type of dipeptidase cleaving a dipeptide bond with a prolyl residue at the carboxyl terminus, X-Pro (Ref). This enzyme has a wide range of substrate specificity against various substrates, including the fluoride containing chemical warfare (CW) nerve agents, soman (GD: O-pinacolylmethylphosphonofluoridate), sarin (GB: O-isopropyl methylphosphono-fluoridate), GF (O-cyclohexyl methylphosphono-fluoridate), and cyanide containing tabun (GA: ethyl N,N-dimethylphosphoramidocyanidate). Here again, the polymer-enzyme conjugate is formed by first dissolving the polymer in an appropriate solvent, and then adding the enzyme to said solution, whereby the enzyme is automatically encapsulated by the polymer. The solution can then be dried to recover the nanoencapsulated polymer-enzyme conjugate.

Enzymatic Assays

Enzyme activity against diisopropylfluorophosphate (DFP) was assayed by monitoring fluorine release with an ion-specific electrode following a modified method as described previously. See Cheng, Tu-Chen, Harvey, S. P., and A. N. Stroup, "Purification and Properties of a Highly Active Organophosphorus Acid Anhydrolase from *Alteromonas undina*," Appl. Environ. Micro. Vol. 59, 3138–3140 (1993) and, Cheng, Tu-Chen, Harvey, S. P., and G. L. Chen, "Cloning, Expression, and Nucleotide Sequence of a Bacterial Enzyme for Decontamination of Organophosphorus Nerve Agents," Appl. Environ. Micro. Bol. 62, 1636–1641 (1996) both of which are incorporated by reference herein. The reaction medium contained 50 mM $(NH_4)_2CO_3$ (pH 8.7), 0.1 mM $MnCl_2$, 3 mM DFP, and 5–25 µl of the enzyme (0.3–0.4 U) in a total volume of 2.5 ml. Results were corrected for spontaneous hydrolysis under identical conditions. One unit (U) of enzyme catalyzes the release of 1.0 µmole of fluorine per minute at 25° C. Specific activity is expressed as Units per mg of protein. Protein concentration was determined using Pierce Coomassie protein assay reagent and bovine serum albumin to generate a standard curve.

Growth of the Recombinant Clone pTCJS4/XL1

The recombinant clone pTCJS4/XL1 for A. spJD6.5 prolidase production was grown in LB medium containing 100 µg/ml ampicillin as reported previously in Cheng, Tu-Chen., Liu, L., Wang, B., Wu, J., DeFrank, J. J., Anderson, D. M., Rastogi, V. K., and A. B. Hamilton, "Nucleotide Sequence of a Gene Encoding an Organophosphorus Nerve Agent Degrading Enzyme from *Alteromonas haloplanktis*", J. Ind. Micro. Vol. 18, 49–55 (1997) and, Cheng, Tu-Chen., Rastogi, V. K., DeFrank, J. J., and G. W. Sawiris, "G-Type Nerve Agent Decontamination by Alteromonas Prolidase", Annals. N. Y. Acad. Sci. Vol. 864, 253–258 (1998) both incorporated by reference herein, and the cells were harvested 6 hours after IPTG induction.

A. spJD6.5 Prolidase Purification

Cells (2 L) were disrupted by two passages through a French pressure cell. The cell debris was removed by centrifugation, see Cheng et al, 1996, as previously cited. With a non-optimized, single-batch incubation of cells in a shaker flask, the yield of enzyme reached at 150–200 mg/L of culture after 6 h of IPTG induction corresponding to 50–60% of the total cellular protein. The large-scale production of OPAA is the first key step in the development of a new generation of chemical warfare decontamination and protection systems.

The crude lysate was then fractionated with $(NH4)_2SO_4$ at 40–65% saturation and loaded onto Q-Sepharose column (3×14.5 cm), following the procedure similar to those described previously (Cheng et al., 1997, as previously cited. After unbound proteins were removed by washing with 0.2 M NaCl in 10BM buffer (10-mM Bis-tris propane, pH 7.2, containing 0.1 mM $MnCl_2$), enzyme was eluted with a linear gradient of 0.2 to 0.6 M NaCl in the same buffer. A. spJD6.5 prolidase eluted at approximately 400 mM NaCl. Fractions containing A. spJD6.5 prolidase were pooled, concentrated with $(NH_4)_2CO_3$ at 65% saturation and dialyzed against 10 BM buffer.

Preparation of Nanoencapsulated Enzymes

A ratio of twenty µg nanocapsule polymers (HBPs) and 1 µg A. spJD6.5 prolidase were mixed in 100 µl BM buffer. The enzyme-polymer solution and their lyophilized powder were assayed in various conditions. Producing the nanoencapsulated enzymes is accomplished by simply mixing the polymers and enzyme in buffer solution whereby the enzyme is encapsulated, and then drying the solution to make powder. The powder can then be stored until delivery of the enzyme is needed.

While the invention has been described in this specification with some particularity, it will be understood that it is not intended to limit the invention to the particular embodiments provided herein. On the contrary, it is intended to cover all alternatives, modifications, and equivalents as may be included within the spirit and scope of the invention as defined in the appended claims.

What is claimed is:

1. A nanoencapsulated biomolecule, consisting essentially of:
   (a) a nanocapsule having a core-shell structure, wherein said nanocapsule consists essentially of randomly branched hydrophilic polymer having hydrophobic chain-end moieties; and
   (b) a bioactive molecule encapsulated within said nanocapsule.

2. The nanoencapsulated biomolecule of claim 1, wherein said nanocapsules have a core-shell structure wherein the location of said chain-end moieties in said structure will vary depending upon environmental conditions.

3. The nanoencapsulated biomolecule of claim 1, wherein said hydrophilic polymer comprises randomly branched polyoxazoline polymer.

4. The nanoencapsulated biomolecule of claim 3, wherein said polyoxazoline polymer comprises polyethyloxazoline polymer.

5. The nanoencapsulated biomolecule of claim 4, wherein said polyethyloxazoline polymer comprises poly (2-ethyloxazoline) polymer.

6. The nanoencapsulated biomolecule of claim 1, wherein said hydrophilic polymer comprises randomly branched polyethyleneoxide (PEO) polymer.

7. The nanoencapsulated biomolecule of claim 1, wherein said hydrophobic chain-end moieties are selected from the group consisting of hydrocarbon chains, fluorocarbon chains, and aromatic compounds.

8. The nanoencapsulated biomolecule of claim 7, wherein said hydrocarbon chain comprises a hydrocarbon chain having 6 to 22 carbon atoms.

9. The nanoencapsulated biomolecule of claim 8, wherein said hydrocarbon chain comprises a hydrocarbon chain having 12 to 22 carbon atoms.

10. The nanoencapsulated biomolecule of claim 9, wherein said hydrocarbon chain comprises a hydrocarbon chain having 18 carbon atoms.

11. The nanoencapsulated biomolecule of claim 1, wherein said nanoencapsulated biomolecule has a size in the range of from about 10–500 nanometers.

12. The nanoencapsulated biomolecule of claim 11, wherein said nanoencapsulated biomolecule has a size of about 200 nanometers.

13. The nanoencapsulated biomolecule of claim 1, wherein said nanocapsules and said nanoencapsulated biomolecules are soluble in aqueous and organic solvents.

14. The nanoencapsulated biomolecule of claim 1, wherein said nanoencapsulated biomolecule is stable in pH in the range of from about 2–12.

15. The nanoencapsulated biomolecule of claim 1, wherein said nanoencapsulated biomolecules are stable at temperatures of from about −40° C. to about 60° C.

16. The nanoencapsulated biomolecule of claim 1, wherein said nanoencapsulated biomolecules are stable in blood circulation in vivo.

17. The nanoencapsulated biomolecule of claim 1, wherein said nanoencapsulated biomolecule is lyophilized to a dry powder.

18. The nanoencapsulated biomolecule of claim 17, wherein said dry powders are stable from −40° C. to 100° C.

19. The nanoencapsulated biomolecule of claim 1, wherein said nanocapsule is temperature sensitive such that said nanocapsule contracts at higher temperatures and expands at lower temperatures.

20. The nanoencapsulated biomolecule of claim 1, wherein release of said bioactive molecule from said nanocapsule is temperature sensitive such that release can be controlled by changing temperature.

21. The nanoencapsulated biomolecule of claim 1, wherein said hydrophobic chain-end moieties of said nanocapsule change location in the core-shell structure depending upon solvent polarity, thereby changing the size and shape of said nanocapsule.

22. The nanoencapsulated biomolecule of claim 1, wherein said bioactive molecule is selected from the group consisting of proteins, enzymes, antibodies, peptides, DNA, RNA, gene fragments, and small molecule drugs.

23. The nanoencapsulated biomolecule of claim 22, wherein said enzyme comprises organophosphorus acid anhydrolase (OPAA).

24. The nanoencapsulated biomolecule of claim 22, wherein said small molecule drug is selected from the group consisting of atropine and pyridine-2-aldoxime methchloride (2-PAM).

* * * * *